United States Patent
Hodson et al.

(10) Patent No.: US 8,406,521 B2
(45) Date of Patent: Mar. 26, 2013

(54) OCR INTERFACE TO SINGLE RESULT DIAGNOSTIC INTERFACE

(75) Inventors: Robert P. Hodson, Hartford, WI (US); Charles Cameron Brackett, Pewaukee, WI (US)

(73) Assignee: Honeywell International Inc., Morristown, NJ (US)

(*) Notice: Subject to any disclaimer, the term of this patent is extended or adjusted under 35 U.S.C. 154(b) by 492 days.

(21) Appl. No.: 12/559,051

(22) Filed: Sep. 14, 2009

(65) Prior Publication Data

US 2011/0064283 A1 Mar. 17, 2011

(51) Int. Cl.
*G06K 9/00* (2006.01)
(52) U.S. Cl. ......... 382/181; 382/128; 382/132; 382/154
(58) Field of Classification Search .................. 382/128, 382/132, 133, 154, 181, 195, 294
See application file for complete search history.

(56) References Cited

U.S. PATENT DOCUMENTS

| | | | | |
|---|---|---|---|---|
| 5,802,361 | A | * | 9/1998 | Wang et al. .................... 382/217 |
| 5,814,798 | A | * | 9/1998 | Zancho .......................... 235/380 |
| 5,889,506 | A | * | 3/1999 | Lopresti et al. ................ 345/158 |
| 6,418,424 | B1 | * | 7/2002 | Hoffberg et al. ................. 706/21 |
| 2004/0186357 | A1 | * | 9/2004 | Soderberg et al. ............. 600/300 |
| 2005/0288571 | A1 | * | 12/2005 | Perkins et al. ................. 600/407 |
| 2006/0200253 | A1 | * | 9/2006 | Hoffberg et al. ................ 700/19 |
| 2007/0055128 | A1 | * | 3/2007 | Glossop ......................... 600/407 |
| 2007/0070038 | A1 | * | 3/2007 | Hoffberg et al. .............. 345/156 |
| 2008/0281167 | A1 | * | 11/2008 | Soderberg et al. ............. 600/300 |
| 2010/0324380 | A1 | * | 12/2010 | Perkins et al. ................. 600/301 |

* cited by examiner

Primary Examiner — Vu Le
Assistant Examiner — Aklilu Woldemariam
(74) Attorney, Agent, or Firm — Husch Blackwell LLP

(57) ABSTRACT

A method and apparatus are provided. The method includes the steps of an imaging device capturing an image of a display of a medical instrument, an image processor determining a location of a patient biometric measurement within the image, an optical character recognition module recognizing a set of alphanumeric characters within the determined location and a communication processor sending the recognized characters to a remotely located healthcare database.

20 Claims, 2 Drawing Sheets

OCR INTERFACE TO SINGLE RESULT DIAGNOSTIC INTERFACE

FIELD OF THE INVENTION

The field of the invention relates to communication interfaces and more particularly to communication interfaces for remotely operated medical devices.

BACKGROUND OF THE INVENTION

There are many biometric measuring devices in the marketplace today. While the use of these devices by physicians is fairly straightforward, many of these devices may also be used by in-home nurses for the disabled or for elderly people who are shut-in. When used in the home, the readings may be reported to an appropriate health reporting agency. In order to ensure the proper reporting of readings, many of these devices are provided with a communication interface that connects to the health reporting agency through the telephone system.

Most biometric devices used in the home have their own proprietary interfaces to transfer the reading from the biometric device to a hub or IT system of the health agency. The existence of the different interfaces is a significant problem for health agencies because it can be very costly to maintain and develop the interfaces for a large number of different biometric devices.

One type of biometric device that is in common use by healthcare professionals is the glucometer. There are literally dozens of different glucometers on the market today, with dozens more that have been made obsolete.

A number of health reporting agencies (e.g., HoMed) currently provide support for home-bound elderly people through the use of biometric meters that receive and report results through the telephone system. Because of the expense, most agencies choose only a few of the most frequently used biometric devices and proceed to develop interfaces for those chosen devices.

In general, the elderly could benefit from a greater availability of biometric devices with a standard interface. However, there is very little agreement among manufacturers as to how to develop a standardized interface. Accordingly, a need exists for better methods of interfacing biometric devices.

DETAILED DESCRIPTION OF AN ILLUSTRATED EMBODIMENT

Figure 1:
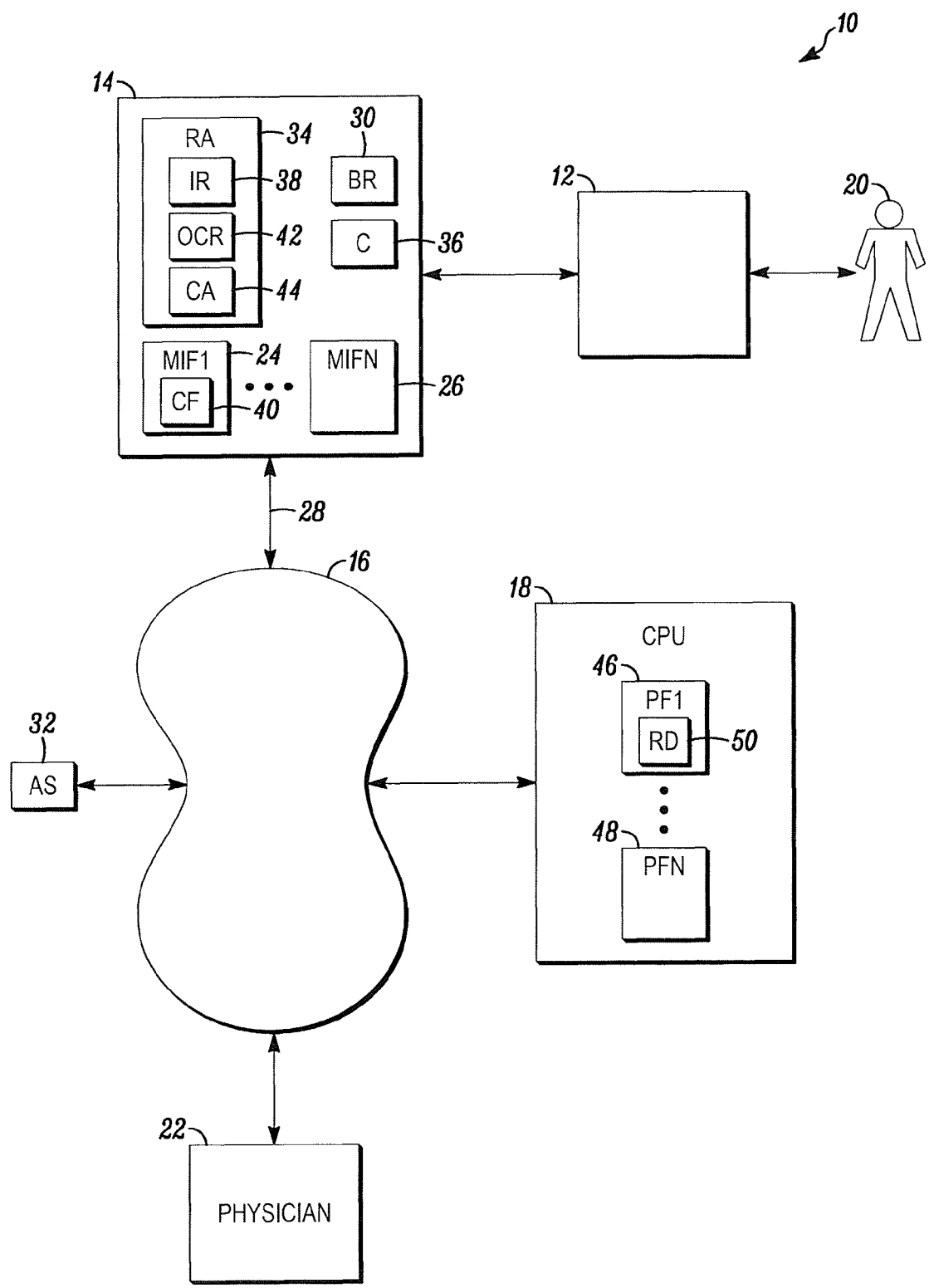
FIG. 1 is a block diagram of a patient reporting system in accordance with an illustrated embodiment of the invention.

FIG. 1 is a block diagram of a biologic reporting system 10 shown generally in accordance with an illustrated embodiment of the invention. The reporting system 10 may be used by a home-bound patient 20 to report on the patient's health to a central database 18 and may also be used by a physician 14 to track the patient's health through the database 18.

Included within the system 10 may be one or more medical measuring devices 12 used by the patient 20 to measure health parameters of the patient 20. The measuring device 12 may be embodied as any of a number of different types of devices used to measure the biologic parameters (e.g., a glucometer, blood pressure measurement device, blood oxygen level measurement device, etc.) of the patient 20.

The system 10 also includes an imaging device (e.g., a cellphone) 14 used to capture image information from the measuring device 12. The use of the imaging device 14 avoids the need for complicated hardware and software that would otherwise be needed to retrieve readout information from any of the different types of medical measurement devices 12 that could be used by a patient 20. In this case, instead of requiring complicated hardware and software to interface with the many different measuring devices 12, the imaging device 14 simply captures image information from a readout of the various devices 12.

In this regard, the imaging device 14 may contain one or more imaging files 24, 26 including a file provided for each separate measuring device 12 or family of devices 12 used by the patient 20. Included within each of the imaging files 24, 26 may be characteristics used to identify the device 12 as well as characteristics of the device 12 that allow information from a readout of to be optically retrieved. The identifying characteristics of the device 12 may include information that defines an overall shape of the device 12 and/or any special markings (e.g., trademark, model number, manufacturer's name, general layout of a faceplate, etc.).

The device readings characteristics of the device 12 may include a relative location of a readout (i.e., a display) on the device as well as a format of the display. For example, a date and time may be located in an upper right corner of a read-out screen in a 10 point font scale, while a patient biometric measurement (e.g., temperature) may be displayed in a center in a 16 point font with a reading scale (e.g., centigrade, Fahrenheit) located in right side in 10 point font.

The imaging device 14 may be connected and report information to the database 18 through a public communication system (e.g., the public switch telephone network (PSTN), the Internet, etc.) 16. A wireless interface 28 may connect the imaging device 14 to a wireless base station of the public communication network 16.

In order to use the system 10, a user of the imaging device 14 may activate a browser 30 and download a reporting application (processor) 34 from an application storage website 32 through the public communication network 16 into a persistent memory of the imaging device 14. The user may install the application 34 on the imaging device 14 and activate the reporting processor 34 as appropriate.

Upon activation, the application 34 may first query the user as to the type of device 12 to be read. Alternatively, the processor 34 may present a menu of possible types of devices 12. Upon selection of a type of device 12, the processor may connect to the website 32 and download a second menu for selection of a specific model. The user may select a specific model and the processor may download the appropriate imaging file 24, 26 that corresponds to the device 12. The user may repeat this process for each specific device 12 to be used by the patient 20.

The reporting processor 34 may operate in the background or may only be activated when a need arises for reporting a measurement from the patient 20. When operating in the background, the processor 34 may generate audible and/or visual reminders to notify the patient 20 whenever a measurement is needed.

In either case and at the desired time, the user may collect a measurement via the measuring device 12 using processes established by a manufacturer of the device 12. If the device 12 is a blood oxygen sensor, then the user may insert his/her finger into an optical detection device and the device may collect a reading. Similarly, if the device 12 is a glucometer, then the device 12 may determine a blood sugar level from the patient 20 using procedures established by a manufacturer of the device 12.

Figure 2:
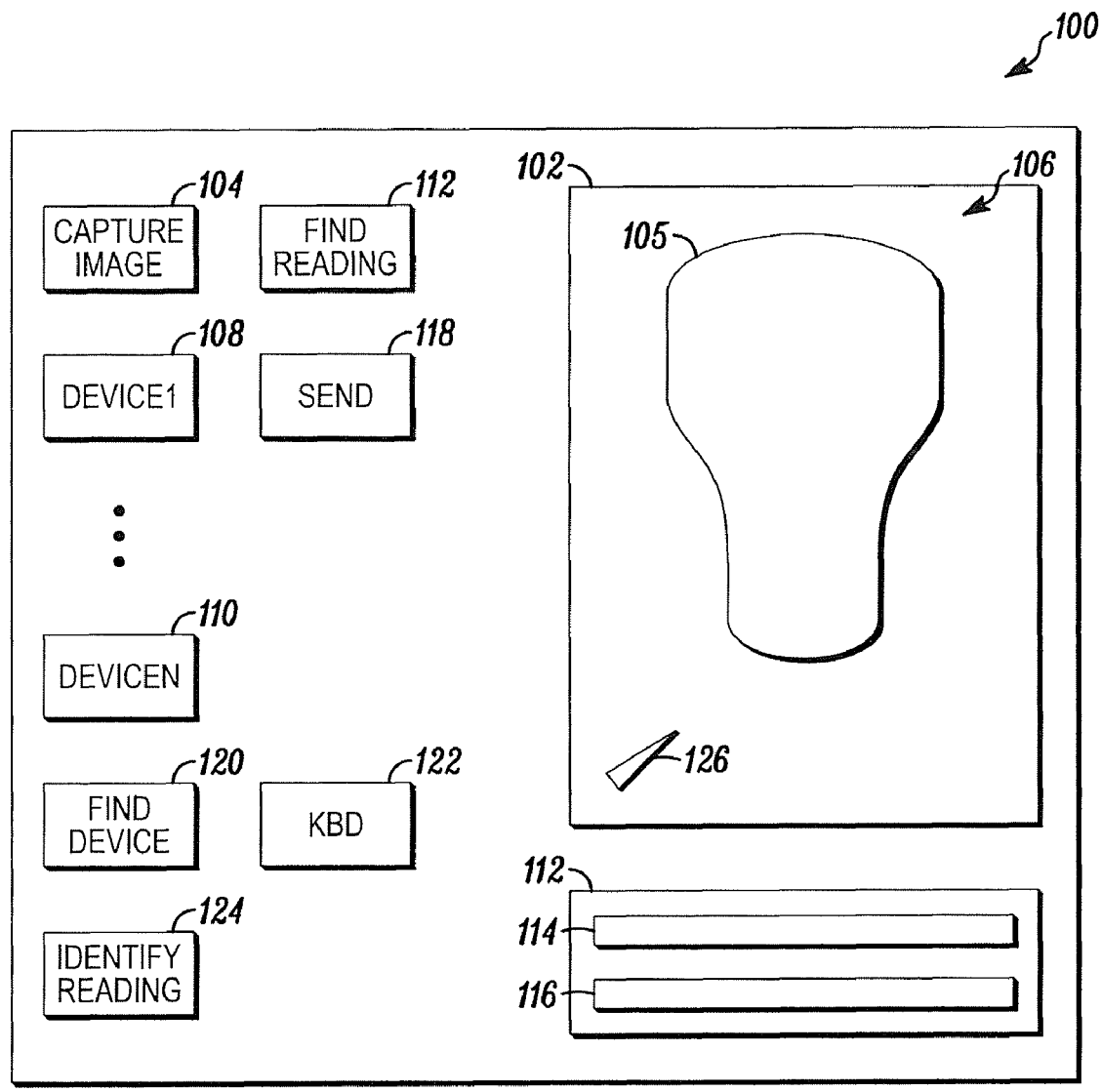
FIG. 2 depicts a control panel that may be used with the system of FIG. 1.

In order to report the reading, the patient 20 or caregiver, may use the imaging device 14 to capture the reading and forward the reading to the database 18. In this regard, the patient 20 may activate a reporting icon on a display of the imaging device 14 to activate the reporting processor 34. In response, a reporting processor control screen 100 (FIG. 2) may be presented on a display of the imaging device 14.

To capture an image, the patient 20 or caregiver may direct a digital camera 36 of the imaging device 14 towards the measuring device 12. In response, an image 106 of the measuring device 12 may appear in real-time on a portion of a display of the control screen 100. The patient 20 may center the image and activate the capture image softkey 104. In response, the camera 36 captures the image 106.

The patient 20 may also identify the device 12 to the imaging device 14. The patient 20 may identify the device 12 to the imaging device 14 by selecting a softkey 108, 110 that identifies the device 12. This may be important where the patient 20 uses a number of different types of measuring devices on a daily or weekly basis. The identification of the device 12 by selection of an identifying softkey 108, 110 may be performed before capturing the image 106 or after.

The patient 20 may also activate a find reading softkey 112 to recover the actual biometric reading from the image 106. It should be noted in this regard that if the patient 20 were to only use one measuring device 12, then the steps of identifying the device 12 through softkeys 108, 110 and finding the reading through selection of the softkey 112 could be combined into a single softkey (e.g., the capture image softkey 104).

In response to activation of the find reading softkey 112 (or the capture image softkey 104 if only a single measurement device 12 is used), an image recognition processor 38 is activated to process the captured image 106. In response, the image recognition processor 38 retrieves the image file 24, 26 identified by the device identification softkeys 108, 110 (or the single image file 24, 26 if only a single device 12 is used) and uses the content of the file 24, 26 to recover a reading from the image 106.

As a first step, the image recognition processor 38 may localize the device 12 within the captured image 106. For example, a set of edge detecting and scaling tools may be used to locate and match the device 12 within the captured image with a reference image within the image file 24, 26. In addition to matching the outline of the device 12 from the image file 24, 26, the image recognition processor may also operate to recognize and match graphic images on face of the device 12 such as model numbers, trademarks or general layouts of operational features such as control buttons and display screens.

Once the image recognition processor 38 identifies the device 12, the processor 38 may retrieve the coordinates and features 40 of the biometric reading on a face of the device 12. In this case, the coordinates of the coordinates and features 40 define the relative location of the biometric measurement relative to a salient feature of the identified image 105 of the device 12. For example, the coordinates may identify the four corners of a display relative to a top edge and relative to a left side of the identified image 105.

The image recognition processor 38 may pass the coordinates and features 40 to an optical character recognition (OCR) processor 42. Within the OCR processor 42, one or more coordinates of the coordinates 40 may be used to identify respective fields that are to be read by the OCR processor 42. In this regard, the features 40 may identify the units of measurement of the measurement device 12. Alternatively, one coordinate set of the coordinates 40 may identify a first field displaying a numeric measurement value and a second coordinate set of the coordinates 40 may identify a second field that displays the units of measurement of the first field. Similarly, a first feature of the features 40 may identify a font of the first field and a second feature of the features 40 may define a font of the second field.

Upon receiving the coordinates and features 40, the OCR processor 42 retrieves the pixels corresponding to the coordinates 40 and converts the pixel content into a set of alphanumeric characters. The OCR processor 42 may also add a time stamp if the device 12 does not include a time display within the image 105.

In addition to recognizing the reading within the image 105, the OCR processor 42 may display the recognized reading in a local display 112. In this case, the OCR processor 42 may display the reading in a first window 114 and any other information (e.g., units, time, etc.) in a second window 116.

The patient 20 may review the display 112. If the display shows correct readings, then the patient 20 may activate a send softkey 118.

Upon activation of the send softkey 118, a communications processor 44 may retrieve the reading and compose a packet message transferring the reading to the database 18. In this case, the communications processor may incorporate the reading into an e-mail or instant message along with an identifier of the patient 20 or identifier (e.g., electronic serial number) of the imaging device 15.

Within the database 18, a processor may process the received packet. In this case, the processor may identify the patient from a source address of the packet and/or identifier of the patient and save the packet 50 in a file 46, 48 designated for the patient 20.

In another embodiment of the invention, the imaging device 14 may be provided in the form of a laptop or desktop computer combined with an imaging device 36. The embodiment has the advantage of being able to combine the reporting features with additional in-home patient care features.

In another embodiment, reporting processor 34 of the imaging device 14 may be provided with additional features to help elderly patients 20 download imaging files 24, 26 for use with the imaging device 14. For example, the imaging device 14 may be provided with a keyboard 132 through which the patient 20 or caregiver can enter a name and model number of a measurement device 12. Once a name and model number has been entered, the user may activate a find device softkey 120 to send the information back to the website 32. Within the website, the information may be used to identify and download the appropriate image file 24, 26 to the imaging device 14.

In another alternative, the reporting processor 34 may be provided with features to automatically download image files 24, 26 automatically. In this case, the user may simply activate the capture image softkey 104 followed by the find device softkey 120. In this case, the communication processor 44 may upload the content of the display 102 to the website 32. In this case, an image processor located at the website 32 may compare the content of the display 102 with images of many different measurement devices 12 until a match is found. When a match is found, then the website 32 may download the appropriate image file 24, 26 to the imaging device 14 and the device 14 may operate as discussed above.

In still another embodiment, the imaging device 14 may be provided with features to collect and send readings to the database 18 without any requirement for an image file 24, 26.

In this case, the user may capture the image via the softkey 104. The user may then use the keyboard 122 to place and drag a cursor 126 across the reading within the image 105 in order to identify the portion of the display 102 that contains the reading. The user may then activate the find reading softkey 112 to cause the OCR processor 42 recognize any reading within the identified area.

A specific embodiment of a reporting system for reporting biometric readings of home-bound patients has been described for the purpose of illustrating the manner in which the invention is made and used. It should be understood that the implementation of other variations and modifications of the invention and its various aspects will be apparent to one skilled in the art, and that the invention is not limited by the specific embodiments described. Therefore, it is contemplated to cover the present invention and any and all modifications, variations, or equivalents that fall within the true spirit and scope of the basic underlying principles disclosed and claimed herein.

The invention claimed is:

1. A method comprising:
    a cellphone having an input receiving an identifier of a medical instrument;
    an image processor of the cellphone retrieving a device file containing characteristics of the medical instrument based upon the received identifier;
    the image processor of the cellphone retrieving a set of coordinates of a biometric readout located on a display of the medical instrument from the retrieved file;
    a camera of the cellphone capturing an image of a display of the medical instrument;
    the image processor localizing an outline of the display of the medical instrument within the image;
    the image processor determining a location of respective fields of a patient biometric measurement within the outline of the image at least from the set of coordinates;
    an optical character recognition module recognizing a set of alphanumeric characters within the respective fields at a location of the coordinates within the image; and
    a communication processor of the cellphone sending the recognized characters to a remotely located healthcare database.

2. The method as in claim 1 wherein the step of determining the location of the measurement further comprises using pattern matching.

3. The method as in claim 1 further comprising providing a plurality of image files of medical instruments and matching at least one of the plurality of image files with the captured image.

4. The method as in claim 3 further comprising retrieving the location of the patient measurement from the matched file.

5. The method as in claim 1 wherein the step of determining the location of the measurement further comprises an operator identifying the measurement with a cursor.

6. The method as in claim 1 further comprising incorporating the recognized characters into an instant message for transmission to the database.

7. A apparatus comprising:
    an imaging device, the imaging device further comprises:
    an input of the imaging device that receives an identifier of a medical instrument from a user;
    an image processor that retrieves a device file containing characteristics of the medical instrument, the characteristics including at least a set of coordinates of a readout located on a display of the medical instrument;
    a camera that captures an image that includes a display of the medical instrument, wherein the image processor localizes an outline of the display of the medical instrument within the captured image and determines a location of a patient biometric measurement within the outline of the medical instrument at least from the set of coordinates;
    an optical character recognition module that recognizes a set of alphanumeric characters displayed on the medical instrument at the coordinates of the readout; and
    a communication processor that sends the recognized characters to a remotely located healthcare database.

8. The apparatus as in claim 7 further comprising an image file of the medical instrument that the image processor compares with the captured image.

9. The apparatus as in claim 8 further comprising a set of coordinates within the image file that identifies a location on a display of the medical instrument on the located image of the medical instrument.

10. The apparatus as in claim 8 further comprising a set of coordinates within the image file that identifies locations of a plurality of fields provided on a display of the medical instrument within the located image of the medical instrument.

11. The apparatus as in claim 7 further comprising a cellular telephone.

12. The apparatus as in claim 11 further comprising a reporting application downloaded to and saved on a non-transitory computer readable medium of the cellular telephone from a website accessed through the cellular telephone or from a personal computer via a USB or Bluetooth connection.

13. The apparatus as in claim 7 further comprising an e-mail sent to the database that incorporates the recognized characters.

14. The apparatus as in claim 7 further comprising an instant message sent to the database that incorporates the recognized characters.

15. A apparatus comprising:
    an imaging device, the imaging device further comprises:
    an input including a plurality of selectable keys, the user identifies a medical instrument to the imaging device via the keys;
    an imaging processor that retrieves a device file of the identified medical instrument, the retrieved file includes at least a set of coordinates of a readout on a display of the medical instrument;
    a camera that captures an image of the medical instrument where at least a portion of the captured image depicts the display of the medical instrument with a biometric measurement of a patient shown on the readout, where the image processor localizes an outline of the display of the medical instrument and where a location of the biometric measurement within the outline of the portion is determined based upon the set of coordinates;
    an optical character recognition module that recognizes a set of alphanumeric characters shown on the readout at the location of the set of coordinates; and
    a packet message incorporating the recognized characters that is sent to a remotely located healthcare database.

16. The apparatus as in claim 15 further comprising a plurality of image files wherein a content of at least one of the plurality of image files matches the medical instrument.

17. The apparatus as in claim 16 wherein at least some of the plurality of files contain coordinates of a display of the medical instrument relative to the portion.

18. The apparatus as in claim 16 further comprising an image processor that determines a location of the medical instrument within the image by matching a content of at least one of the plurality of images files with a content of the portion.

19. The apparatus as in claim 15 wherein the packet message further comprises an identifier of the patient.

20. The apparatus as in claim 15 wherein the packet message further comprises a time of the biometric measurement.

* * * * *